(12) United States Patent
Wiktor et al.

(10) Patent No.: US 10,220,130 B2
(45) Date of Patent: Mar. 5, 2019

(54) DEVICE AND METHOD FOR BALANCING BETWEEN AN INFLOW INTO AND AN OUTFLOW OUT OF A MEDICAL TREATMENT DEVICE

(71) Applicant: Fresenius Medical Care Deutschland GmbH, Bad Homburg (DE)

(72) Inventors: Christoph Wiktor, Gelnhausen (DE); Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 232 days.

(21) Appl. No.: 15/121,141

(22) PCT Filed: Mar. 11, 2015

(86) PCT No.: PCT/EP2015/055074
§ 371 (c)(1),
(2) Date: Aug. 24, 2016

(87) PCT Pub. No.: WO2015/135989
PCT Pub. Date: Sep. 17, 2015

(65) Prior Publication Data
US 2017/0014565 A1 Jan. 19, 2017

(30) Foreign Application Priority Data
Mar. 13, 2014 (DE) .......... 10 2014 003 619

(51) Int. Cl.
*F16K 11/20* (2006.01)
*A61M 1/16* (2006.01)

(52) U.S. Cl.
CPC ..... *A61M 1/1635* (2014.02); *A61M 2205/123* (2013.01); *A61M 2205/128* (2013.01); *A61M 2205/3331* (2013.01)

(58) Field of Classification Search
CPC .............. A61M 1/1601; A61M 1/1635; A61M 1/1639; A61M 1/1647
See application file for complete search history.

(56) References Cited

U.S. PATENT DOCUMENTS

| 4,997,570 | A | * | 3/1991 | Polaschegg | A61M 1/16 210/123 |
| 2002/0088752 | A1 | * | 7/2002 | Balschat | A61M 1/1654 210/646 |

(Continued)

FOREIGN PATENT DOCUMENTS

| DE | 2634238 | 2/1978 |
| DE | 2858205 | 3/1980 |

(Continued)

*Primary Examiner* — Reinaldo Sanchez-Medina
(74) *Attorney, Agent, or Firm* — Jacobson Holman, PLLC.

(57) ABSTRACT

A balancing device and a method for balancing between an inflow into a blood treatment unit of a medical treatment device and an outflow out of the blood treatment unit are disclosed. The balancing device: includes a balancing unit, which has at least one exchange vessel; means for conveying fluid into and/or out of the exchange vessel and means for interrupting the inflow of fluid into the exchange vessel and/or the outflow of fluid out of the exchange vessel; and a control unit for controlling the means for conveying fluid and the means for interrupting the inflow and/or outflow of fluid by an equalization of pressure between a first work cycle and a second work cycle.

13 Claims, 8 Drawing Sheets

(56) References Cited

U.S. PATENT DOCUMENTS

| | | | | |
|---|---|---|---|---|
| 2002/0107474 | A1* | 8/2002 | Noack | A61M 1/28 604/29 |
| 2006/0047193 | A1* | 3/2006 | Zhang | A61M 1/16 600/368 |
| 2006/0254982 | A1* | 11/2006 | Kopperschmidt | A61M 1/342 210/646 |
| 2009/0124963 | A1 | 5/2009 | Hogard et al. | |
| 2009/0198170 | A1 | 8/2009 | Childers et al. | |
| 2010/0016777 | A1* | 1/2010 | Burbank | A61M 1/16 604/5.04 |
| 2013/0023812 | A1* | 1/2013 | Hasegawa | A61M 1/342 604/6.09 |

FOREIGN PATENT DOCUMENTS

| | | |
|---|---|---|
| DE | 19702211 | 7/1998 |
| DE | 102010023635 | 12/2011 |

\* cited by examiner

DEVICE AND METHOD FOR BALANCING BETWEEN AN INFLOW INTO AND AN OUTFLOW OUT OF A MEDICAL TREATMENT DEVICE

TECHNICAL FIELD

The invention relates to the field of balancing equipment for a medical treatment device, in particular for balancing dialysis fluid between an inflow into a dialyzer and an outflow out of the dialyzer.

BACKGROUND

There are various known types of treatment devices, which have a treatment unit that is to be supplied with fluid. The known treatment devices include the blood treatment machines, for example. Various blood purification methods, which are performed in an extracorporeal circulation, have thus become known in kidney replacement therapy, involving the removal of substances that must be eliminated in urine from the blood, i.e., blood constituents, which are eliminated through the kidneys in a healthy person.

Other known extracorporeal blood treatment machines include plasma separation systems as well as adsorbers for liver support therapy or for treatment of sepsis.

In hemodialysis, substances that are present in the blood and are normally eliminated in urine undergo diffusive mass transport through a semipermeable membrane into a dialysis fluid. Mass transport takes place through the semipermeable wall of a dialyzer.

The dialyzer has a blood chamber connected to an extracorporeal blood circulation and a dialysis fluid chamber connected to a dialysis fluid circulation. The blood chamber and dialysis fluid chamber are separated from the semipermeable membrane. To prevent diffusive loss of electrolytes that should remain in the blood, the dialysis fluid has a certain composition of electrolytes in a physiological concentration.

In addition, excess fluid is withdrawn through a semipermeable membrane during dialysis, this withdrawal of fluid being accomplished due to the pressure gradient prevailing on the semipermeable membrane.

On the other hand, a convective mass transport additionally takes place through a semipermeable membrane of a filter in hemofiltration, in which a pressure gradient on the membrane is also the driving force for the mass transport.

To balance a loss of desired blood constituents, the electrolytes lost through the membrane must be replaced by a substitute fluid. A combination of convective transport and diffusive transport is referred to as hemodiafiltration. In the context of the present patent application, with the known methods and dialysis equipment, the concept of dialysis or a dialysis treatment should be understood to include both purely diffusive dialysis and hemodiafiltration. Because of the large amounts exchanged, there is a need for accurate balancing of the fluid withdrawn from the patient and the fluid supplied to the patient over the entire duration of the treatment. Gravimetric and volumetric balancing devices are known from the state of the art.

Balancing devices using balancing chambers using separation elements and balancing devices using exchange vessels are known for volumetric balancing.

A dialysis machine having a balancing device which uses balancing chambers is known from DE 26 34 238 A1, for example. With the known hemodiafiltration machine, the balancing device has a hollow body with a rigid volume, which is subdivided by a movable separation element into a chamber for fresh dialysate and a chamber for spent dialysate. The chamber for fresh dialysate is connected by an inlet line to a source for fresh dialysate and to an outlet line through which fresh dialysate is supplied to the dialyzer. The chamber for spent dialysate is connected via an inlet line from which spent dialysate can flow into the chamber and to an outlet line leading to an outlet for the dialysis fluid. In addition, pumps are provided for conveying both fresh and spent dialysis fluid, and a control unit is provided, which allows filling of the two chambers in alternation. The balancing accuracy here is based on the fact that the chamber for spent dialysate and the chamber for fresh dialysate have the same volume. Balancing chambers are therefore usually manufactured with a low manufacturing tolerance using materials that have good volume constancy.

An alternative method for volumetric balancing is based on the use of exchange vessels. An exchange vessel here can be connected via fluid-carrying lines to a source for fresh dialysis fluid, to an outlet for the spent dialysis fluid, to an outlet into the dialyzer into an inlet from the dialyzer. Shut-off elements or valves are provided in the fluid-carrying lines and can be controlled in such a way that a first fluid circulation is formed in a first work cycle, connecting the fluid source to an outlet via the exchange vessel, and in a second work cycle a fluid circulation is formed, connecting the outlet of the dialyzer to the inlet into the dialyzer via the exchange vessel.

Spent dialysis fluid thus flows from the exchange vessel into the outlet during the first work cycle and is replaced by fresh dialysis fluid from the dialysis fluid source. In the second work cycle, fresh dialysis fluid flows out of the exchange vessel and into the dialyzer and is replaced by spent fluid from the dialyzer.

In the second work cycle, the amount of fluid flowing out of the dialyzer corresponds to the amount of fluid flowing into the dialyzer, which thus ensures balancing.

The simple design of an exchange vessel allows the dialysis fluid circulation or parts of the dialysis fluid circulation to be designed as disposable items. Such disposable items may preferably be produced from PVC or some other plastic.

The inventors of the present patent application have recognized that, in this case, there may be a mistake in balancing when there is not a constant volume at different operating pressures because of the material used in the exchange chamber.

The inventors of the present patent application have also recognized that there is no constancy of the quantities of fluid due to the compression of the gas bubbles present in the dialysis fluid when the operating pressure changes.

The object of the present invention is therefore to provide a balancing device and a method for balancing with an increased precision in balancing.

SUMMARY

This object is achieved by a balancing device according to Claim 1, a balancing device according to Claim 2, a method for balancing fluids according to Claim 12 and a method for balancing fluids according to Claim 13. Advantageous refinements are described in the dependent claims.

In accordance with the present disclosure, a balancing device is made available for balancing between an inflow into a blood treatment unit of a medical treatment device and an outflow out of the blood treatment unit.

The medical treatment device may be designed as a hemodialysis machine with a dialyzer as the blood treatment unit or as an apheresis machine with a blood treatment unit comprising an adsorber.

The balancing unit has at least one exchange vessel, a first inlet line leading to the exchange vessel for supplying fluid from a fluid source, in particular from a dialysis fluid source, into the exchange vessel and a first outflow line leading away from the exchange vessel for removing fluid from the exchange vessel into a drain.

In addition, the balancing unit has a second outflow line leading away from the exchange vessel for removing fluid from the exchange vessel into the treatment unit and a second inlet line leading to the exchange vessel for supplying fluid from the treatment unit into the exchange vessel.

The balancing unit additionally comprises means for conveying fluid into and/or out of the exchange vessel and means for interrupting the inflow of fluid into the exchange vessel and/or the outflow of fluid out of the exchange vessel as well as a control unit for controlling the means for conveying fluid and a means for interrupting the inflow and/or outflow of fluid.

The control unit is designed to control the means for conveying the fluid and/or the means for interrupting the flow, such that in a first work cycle of successive work cycles, a first fluid circulation is formed, in which spent fluid from the exchange vessel flows into the outflow and is replaced by fresh fluid from the fluid source, and in a second work cycle of the successive work cycles, a second fluid circulation is formed, in which fresh fluid flows out of the exchange vessel and into the treatment unit and is replaced by spent fluid from the treatment unit.

In other words, in the first work cycle, a fluid circulation, which connects the fluid source to the outflow via the treatment unit, is formed, and in a second work cycle, a fluid circulation, which connects the outflow of the blood treatment unit to the inflow into the blood treatment unit via the exchange vessel, is also formed.

The balancing device again has a pressure pickup, which is connected to the control unit for recording the pressure in the exchange vessel, in particular during the first and second work cycles, and in one embodiment also during a third work cycle.

The control unit is again designed to control the means for conveying fluid into and/or out of the exchange vessel and/or the means for interrupting the flow of fluid into the exchange vessel and/or the outflow of fluid out of the exchange vessel with regard to an equalization of pressure between the first and second work cycles.

This may take place in that, in a third work cycle, the first and second outflow lines are shut off and the pressure in the exchange vessel is brought to the higher of the two pressures or the first and the second inlet lines are shut off, and the pressure in the exchange vessel is brought to the lower of the two pressures.

In alternative embodiments, a third work cycle is not necessary. In one of these embodiments, the means for conveying fluid are designed as a pressure-controlled pump, which is controlled in such a way that in the first work cycle, the pressure in the exchange vessel is essentially equal to the pressure in the exchange vessel in the second work cycle, wherein this condition is maintained in particular until the end of the respective work cycle. Alternatively or additionally, a throttle is provided for controlling the flow through the first and/or second outflow lines, wherein the control unit is additionally designed for controlling the throttle, so that the pressure in the exchange vessel in the first work cycle is essentially equal to the pressure in the exchange vessel in the second work cycle, this condition being maintained until the end of the respective work cycle in particular.

In a refinement of the balancing devices described here, the means for conveying fluid into and/or out of the exchange vessel can be connected to the first and second inflow or to the first and second outflow through a fluid-carrying line, such that means for conveying fluid can convey fluid during the first work cycle and during the second work cycle. A single means for conveying both fresh and/or spent fluid is thus sufficient.

In a refinement of the balancing device, the control unit is equipped to convey fluid into and/or out of the exchange vessel using a measurement signal from the pressure pickup.

In an advantageous embodiment, the means for conveying fluid into and/or out of the exchange vessel comprise a pressure-controlled pump, i.e., a pump that is adjustable with regard to a certain pump pressure. In a refinement of this embodiment, the pressure-controlled pump is an impeller pump (e.g., a centrifugal pump) or a diaphragm pump.

A gas-filled equalizing vessel, which is in fluid connection with the exchange vessel, may be provided as the pressure pickup, wherein measuring means for determining the fluid level in the equalizing vessel are provided and wherein the fluid level indicates a measure of the pressure in the exchange vessel.

In one embodiment of the balancing device, the exchange vessel does not maintain a constant volume when there is a change in pressure in the exchange vessel.

In another embodiment of the balancing device, the exchange vessel is designed as a disposable item or as a part of a disposable item.

In addition, at least one of the fluid lines that form an inflow into the exchange vessel or an outflow out of the exchange vessel may be designed as part of a disposable item, preferably as part of the disposable item containing the exchange vessel. One or more of the shut-off organs or valves here may be designed as clamps on the fluid lines.

The balancing device described here may be part of a medical treatment machine, in particular part of a dialysis machine.

In accordance with the present disclosure, a method is made available for balancing between an inflow into a blood treatment unit of a medical treatment device and an outflow out of the blood treatment unit.

Successive first and second work cycles are provided in this method, whereby a first fluid circulation is formed in the first work cycle, spent fluid from an exchange vessel flowing through a first outlet line into an outflow in this fluid circulation, and fresh fluid from a dialysis fluid source flowing after it to restock the exchange vessel through a first inlet line. In the second work cycle, a second fluid circulation is formed, in which fresh fluid flows out of the exchange vessel, through a second outlet line and into the blood treatment unit and is replaced by spent fluid from the blood treatment unit through a second inlet line. The pressure in the exchange vessel is measured during the first and second work cycles. In addition, the means for conveying fluid into and/or out of the exchange vessel and/or means for interrupting the inflow of fluid into the exchange vessel and/or the outflow of fluid out of the exchange vessel with regard to an equalization of pressure between the first and second work cycles are controlled.

This may take place by shutting off the first and second outflow lines in a third work cycle and bringing the pressure in the exchange vessel to the higher of the two pressures or by shutting off the first and second inlet lines and bringing the pressure in the exchange vessel to the lower of the two pressures.

A third work cycle is not necessary in the alternative embodiments. In one of these embodiments, the means for conveying fluid are designed as a pressure-controlled pump.

The pressure-controlled pump is controlled by using the pressure signal, so that the pressure in the exchange vessel during the first work cycle is basically equal to the pressure in the exchange vessel during the second work cycle, wherein this condition is maintained in particular at the end of the respective work cycle.

Alternatively or in addition to this, a throttle for controlling the flow through the first or second outflow lines is provided. In this embodiment, the measured pressure is used to control the throttle or to additionally control the throttles, so that the pressure in the exchange vessel during at least a portion of the first work cycle is essentially equal to the pressure in the exchange vessel in at least a portion of the second work cycle, wherein this condition is to be maintained in particular at the end of the respective work cycle.

The balancing methods can be modified in the same ways or in modifications corresponding to those described in conjunction with the corresponding balancing device.

DETAILED DESCRIPTION OF THE DRAWINGS

Figure 1:
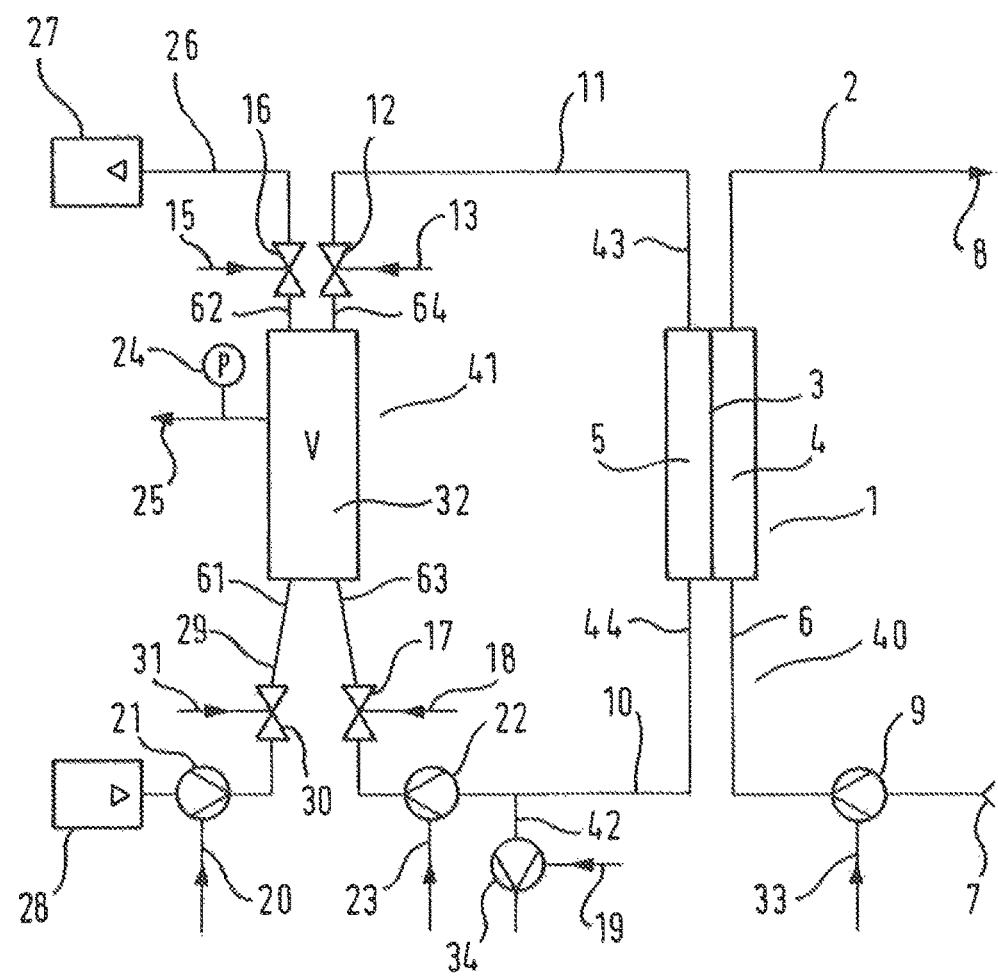
FIG. 1 shows a hemodialysis machine with a dialyzer and a balancing device for balancing between an inflow from the dialyzer and the outflow out of the dialyzer.
Figure 1:
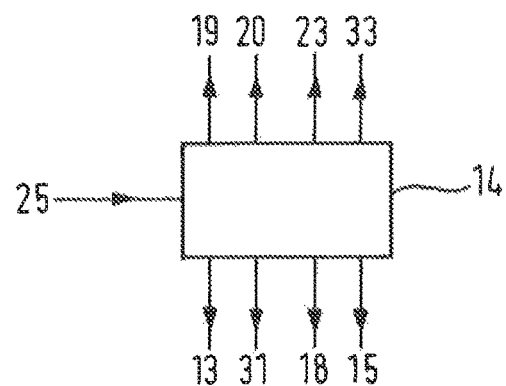

FIG. 1 shows an example of a hemodialysis machine as a blood treatment machine, which has a dialyzer 1 as a blood treatment unit. FIG. 1 shows a greatly simplified schematic diagram illustrating the main components of the hemodialysis machine, including a balancing device 41. The dialysis machine has a dialyzer 1, which is divided by a semipermeable membrane 3 into a blood chamber 4 and a dialysis fluid chamber 5. The balancing device 41 serves to establish a balance between an inflow from the dialyzer 1 and the outflow out of the dialyzer 1 and is a component of the dialysis machine. Blood is taken via an access 7 from the patient to be treated and is connected via a blood inlet line 6 to a blood pump 9 and carried to the blood chamber 4 of the dialyzer 1 via this line. A blood outlet line 2 leads from the blood chamber 4 of the dialyzer, returning the dialyzed blood to the patient through an access 8. During the blood treatment, the patient's blood flows through the blood chamber 4 of the dialyzer 1 in the extracorporeal blood circulation 40.

The dialyzer 1 is supplied with dialysis fluid which flows through the dialysis fluid chamber 5 of the dialyzer 1.

A balancing unit 41, which has an exchange vessel 32, serves for balancing between the dialysis fluid supplied to the dialysis fluid chamber 5 and the dialysis fluid removed from the dialysis fluid chamber 5. The exchange vessel 32 has a first inlet 61 for fresh dialysis fluid and a first outlet 62 for spent dialysis fluid. A second outlet 64 of the exchange vessel 32 leads through the line 11 to an inlet 43 of the dialysis fluid chamber 5. Spent dialysis fluid can flow from the dialysis fluid chamber 5 into the exchange vessel 32 through a second inlet 63 of the exchange vessel 32.

The dialysis fluid is supplied in a dialysis fluid source 28, which may be a canister or a bag. In an alternative embodiment of the dialysis fluid source 28, the dialysis fluid is also prepared during the treatment, i.e., online from corresponding concentrates and pure water (RO water).

A first inlet line 29, which leads to the first inlet 61 of the exchange vessel 32, leads away from the dialysis fluid source 28. A first outflow line 26 leading to a drain or outflow 27, leads away from the first outlet 62 of the exchange vessel. A first dialysis fluid pump 21, which is advantageously designed as a pressure-controlled pump, i.e., a pump that is controlled with regard to its pump pressure is connected to the first inlet line 29 as an impeller pump or as a diaphragm pump, for example. The first dialysis fluid pump 21 delivers fresh dialysis fluid from the dialysis fluid source 28 to the exchange vessel 32.

A second outflow line 11, which leads to an inlet 43 of the dialysis fluid chamber 5 of the dialyzer 1, leads away from the second outlet 64 of the exchange vessel 32. A second inlet line 10 leading to the second inlet 63 of the exchange vessel 32 leads away from the outlet 44 of the dialysis fluid chamber 5 of the dialyzer 1. A second dialysis fluid pump 22, which is advantageously designed as a pressure-controlled pump, for example, as an impeller pump or a diaphragm pump, is connected to the second inlet line 10, delivering spent dialysis fluid from the dialysis fluid chamber 5 into the exchange vessel 32. A pressure pickup, a pressure meter or a pressure gauge 24 is provided for measuring the pressure in the exchange vessel.

The inlet and outlet lines 10, 11, 29, 26 are advantageously designed as hose lines.

The exchange vessel is advantageously designed as a disposable item or as part of a disposable item, which especially advantageously also comprises the inlet and outlet lines.

And ultrafiltration line 42, which is connected to an ultrafiltration pump 34, leads away from the inlet line 10. If the balancing device 41 ensures a good balance between fresh and spent dialysis fluid, then the quantity of liquid withdrawn via the ultrafiltration pump 19 forms a measure of the quantity of fluid withdrawn from the extracorporeal blood circulation through the semipermeable membrane 3 of the dialyzer 1.

The inflow to the exchange vessel 32 may be interrupted by valves 30, 17 of the first inlet line 29 and the second inlet line 10 and can be controlled in this way. On the other hand, the outflow out of the exchange vessel through the valves 16, 12 in the first outflow line 26 and the second outflow line 11 can be interrupted.

The valves 30, 17, 16, 12 are connected to a control unit 14 via control lines 31, 18, 15, 13 and can be controlled by this control unit. The valves 30, 17, 16 and 12 may be designed as electromagnetically operable hose clamps. The first dialysis fluid pump 21 and the second dialysis fluid pump 22 are also connected to the control unit 14 via control lines 20, 23 and can be controlled by this control unit. The pressure pickup, the pressure meter and the pressure gauge 24 are also connected via a data line 25 to the control unit 14 and make available to this control unit measured values for the pressure in the exchange vessel 32. The control unit 14 in the present example is part of the central control unit of the dialysis machine. The central control unit 14 of the dialysis machine is also connected to the ultrafiltration pump 34 via a control line 19 and to the blood pump 9 via a control line 33.

Figure 3:
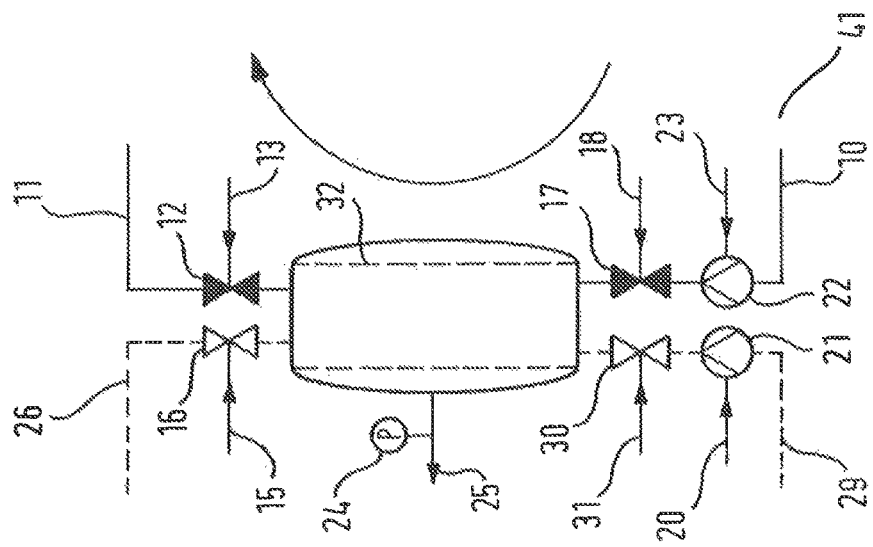
FIG. 3 shows the balancing device from FIG. 1 in a second work cycle of the operating cycle.
Figure 2:
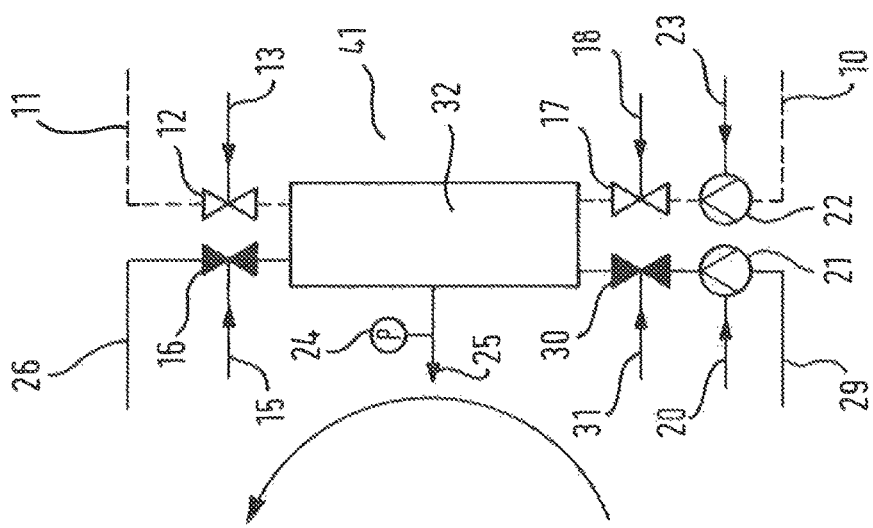
FIG. 2 shows the balancing device from FIG. 1 in a first work cycle of the operating cycle.

The control unit 14 controls the valves 30, 17, 16, 12 and the first dialysis fluid pump 21 and the second dialysis fluid pump 22, so that a first fluid circulation is formed alternately in a first work cycle of successive work cycles; spent fluid flows out of the exchange vessel 32 and into the outflow 27 in this fluid circulation and is replaced by fresh fluid from the dialysis fluid source 28; and in a second work cycle of the successive work cycles, a second fluid circulation is formed, in which the fresh fluid from the exchange vessel 32 flows into the dialyzer and is replaced by spent fluid from the dialyzer, which is described below with reference to FIGS. 2 and 3.

FIG. 2 shows the balancing device 41, which has already been described in conjunction with FIG. 1 during a first work cycle. Elements provided with corresponding reference numerals correspond to those in FIG. 1, to which reference is herewith made instead of repeating the description.

The first work cycle, which is illustrated in FIG. 2, serves to fill the exchange vessel with fresh dialysis fluid from the dialysis fluid source 28. In the first work cycle, which is illustrated in FIG. 2, the dialysis fluid pump 21 pumps fresh dialysis fluid from the dialysis fluid source 28 through the first inlet line 29 into the exchange vessel 32 where it displaces the spent dialysis fluid, which is still in the exchange vessel at the start of the first work cycle and is sent through the first outlet line 26 into the outflow 27. The direction of the arrow shown in FIG. 2 indicates the direction of flow of the dialysis fluid during the first work cycle. During the first work cycle, the valve 30 and the valve 16 are kept open and the valve 17 and the valve 12 are kept closed. Thus, a first dialysis fluid circulation is formed, in which dialysis fluid is circulated through the dialysis fluid pump 20, leading from the dialysis fluid source 28 through the exchange vessel to the outflow. If there is a constant volume of the exchange vessel during the first work cycle, then the quantity of fluid flowing into the exchange vessel from the dialysis fluid source 28 will correspond to the quantity of fluid flowing out into the outflow 27. The first work cycle is advantageously maintained until it can be assumed that the spent dialysis fluid in the exchange vessel 32 has been completely or almost completely displaced by the fresh dialysis fluid by the end of the first work cycle.

The first work cycle is followed by a second work cycle, which serves to fill the dialysis fluid chamber 5 of the dialyzer 1 with fresh dialysis fluid from the exchange vessel. In the second work cycle, which is depicted in FIG. 3, the dialysis fluid pump 22 conveys spent dialysis fluid out of the dialysis fluid chamber 5 through the second inlet line 10 into the exchange vessel 32, where it displaces the fresh dialysis fluid which was in the exchange vessel at the start of the first work cycle and is supplied through the second outflow line 11 of the dialysis fluid chamber 5. The direction of the arrow shown in FIG. 3 indicates the direction of flow of the dialysis fluid during the second work cycle. During the second work cycle, the valve 17 and the valve 12 are kept open and the valve 30 and the valve 16 are kept closed. This forms a second dialysis fluid circulation, in which the dialysis fluid chamber 5 is connected to the exchange vessel 32, and in which dialysis fluid is circulated through the dialysis fluid pump 22.

The first work cycle is advantageously maintained as long as it can be assumed that fresh dialysis fluid is flowing into the dialysis fluid chamber 5 at the end of the second work cycle, and the spent dialysis fluid is displaced completely or almost completely by the fresh dialysis fluid there.

The pressure in the part of the dialysis fluid circulation, which is connected to the exchange vessel 32 during the first work cycle, may be different from the pressure in the part of the dialysis fluid circulation that is connected to the exchange vessel 32 during the second work cycle. In particular the pressure in the exchange vessel 32 during the first work cycle may be different from the pressure in the exchange vessel 32 during the second work cycle. If a constant volume of the exchange vessel is not ensured at different pressures, then the volume of the exchange vessel 32 during the first work cycle may be different from the volume of the exchange vessel during the second work cycle accordingly. A situation in which the pressure in the exchange vessel 32 during the second work cycle is greater than the pressure during the first work cycle is indicated by the exchange vessel, which is represented as being larger in FIG. 3.

If a constant volume of the exchange vessel is not maintained between the first and second work cycles, it may result in an error in balancing in the transition between the first and second work cycles if no additional measures are taken.

To compensate for or prevent such a mistake in balancing, the pressure in the exchange vessel 32 is determined by the pressure pickup, the pressure meter or pressure gauge 24 during the first and/or second work cycle and is transmitted to the control unit 14 over the data line 25. The control unit 14 is also designed to control the dialysis fluid pump 21, the dialysis fluid pump 22, the valve 12 and/or the valve 16 with regard to an equalization of pressure between the first and second work cycles.

In one embodiment, a third work cycle is introduced, in which the valve 16 and the valve 13 are shut off or closed or kept closed, and the pressure in the exchange vessel is brought to a previously measured pressure, wherein the previously measured pressure corresponds to the higher pressures in the exchange vessel during the first work cycle and the second work cycle.

Figure 4:
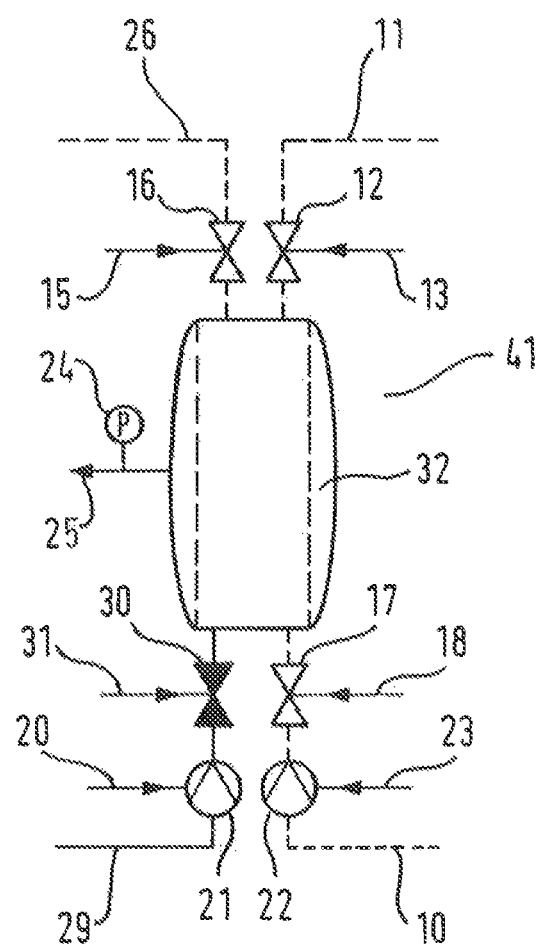
FIG. 4 shows the balancing device from FIG. 1 in a third work cycle.

FIG. 4 shows the situation corresponding to FIGS. 2 and 3, in which a higher pressure prevails in the exchange vessel during the second work cycle than during the first work cycle.

In this case, the inflow from the part of the dialysis fluid circulation that had been connected in the second work cycle is shut off in the third work cycle, i.e., the valve 17 is shut off or closed or kept closed and the dialysis fluid pump 22 is stopped. In addition, the inflow from the part of the dialysis fluid circulation that had been connected in the first work cycle is opened, i.e., the valve 30 is opened or kept open. Through corresponding control of the pressure-controlled dialysis fluid pump 21 (i.e., the dialysis fluid pump, which is in the first work cycle in the dialysis fluid circulation), a pressure is established during the third work cycle in the exchange vessel 32 that corresponds to the pressure during the second work cycle, i.e., the work cycle in which a higher pressure was prevailing in the exchange vessel.

The third work cycle may follow the first work cycle and/or the second work cycle in the chronological order of work cycles.

Figure 5:
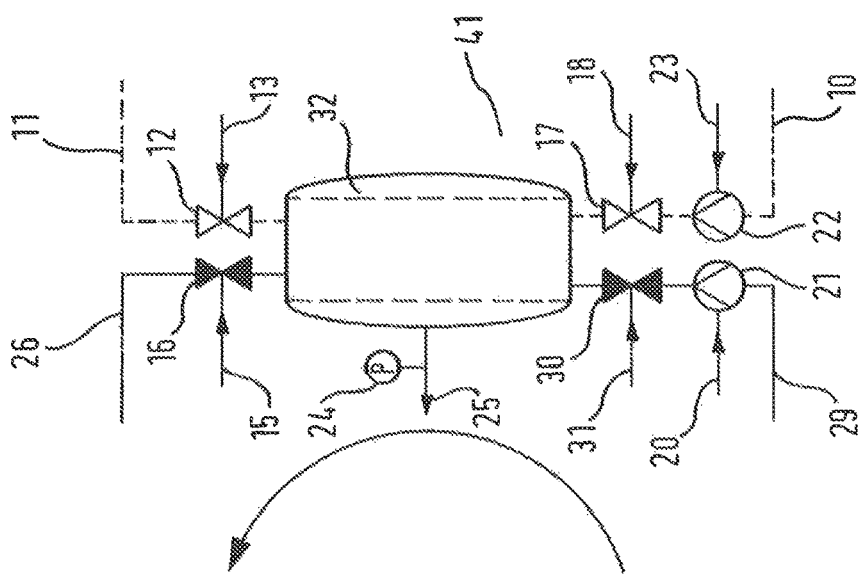
FIGS. 5-7 show additional work cycles of a balancing device.
Figure 6:
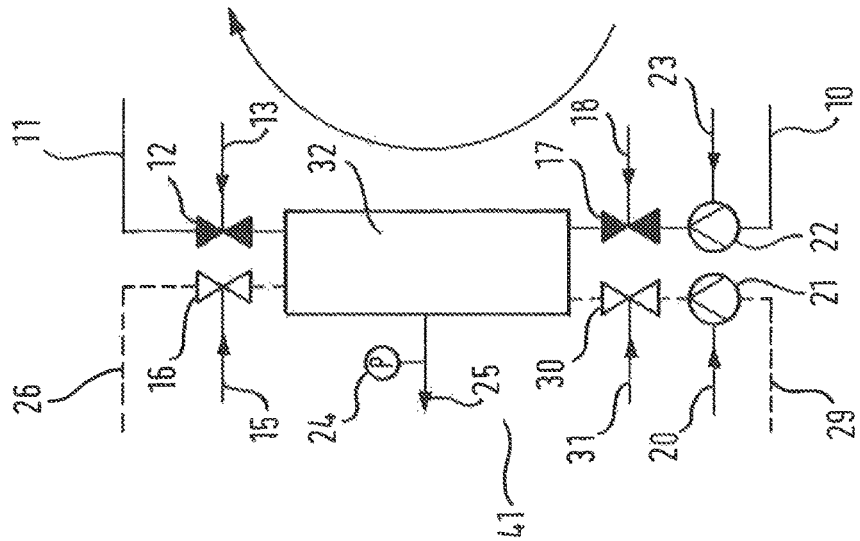

FIGS. 5 and 6 illustrate the situation in which a higher pressure prevails in the exchange vessel during the first work cycle than during the second work cycle, such that the higher operating pressure during the first work cycle is to be increased due to the more voluminous shape of the exchange vessel 32.

Figure 7:
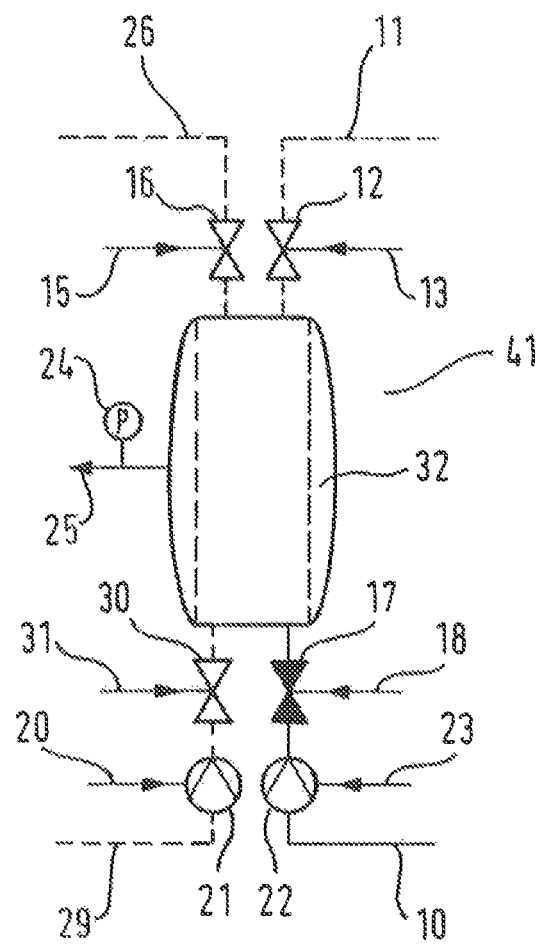

In this case, the inflow from the part of the dialysis fluid circulation that had been connected in the first work cycle is shut off in the third work cycle, which is illustrated in FIG. 7, i.e., the valve 30 is shut off or closed or kept closed and the dialysis fluid pump 21 is shut down. In addition, the inflow from the part of the dialysis fluid circulation that had been connected in the second work cycle is opened, i.e., the valve 30 is opened or kept open. Through corresponding control of the pressure-controlled pump 22 (i.e., the dialysis fluid pump, which is in the second work cycle in the second dialysis fluid circulation), a pressure corresponding to the pressure during the first work cycle is established in the exchange vessel 32 during the third work cycle, i.e., the same work cycle in which a higher pressure prevailed in the exchange vessel.

If one knows in which of the work cycles in normal operation a higher pressure will prevail in the exchange vessel 32 due to the dimensioning of that part of the dialysis fluid circulation that is connected to the exchange vessel in the first work cycle and that part of the dialysis fluid circulation that is connected to the exchange vessel 32 in the second work cycle, then it is sufficient if the pressure in the equalizing vessel is determined in this work cycle.

On the other hand, the pressure conditions in the part of the dialysis fluid circulation containing the dialysis fluid chamber may change during the dialysis treatment and one cannot know for certain from the beginning in which part of the dialysis fluid circulation the higher pressure prevails. In this case, it may be advisable to monitor the pressure in the exchange vessel in both the first work cycle and the second work cycle to ascertain how a pressure equalization is to be accomplished by means of the third work cycle, i.e., whether one should proceed in the manner described in conjunction with FIG. 4 or as described in conjunction with FIG. 7.

In an alternative embodiment, the valve 30 and the valve 17 are shut off or closed or kept closed in the third work cycle and the pressure in the exchange vessel is brought to a previously measured pressure at the output end, whereby the previously measured pressure corresponds to the lower of the pressures in the exchange vessel during the first work cycle and during the second work cycle.

In other words, according to the situation described in conjunction with FIGS. 2 and 3, in which a higher pressure prevails in the exchange vessel during the second work cycle than during the first work cycle, the outflow out of that part of the dialysis fluid circulation that had been connected in the first work cycle is shut off in the third work cycle, i.e., the valve 16 is shut off or closed or kept closed. In addition, the outflow out of that part of the dialysis fluid circulation that had been connected in the second work cycle is opened, i.e., the valve 12 is opened or kept open. Through corresponding control of a pressure-controlled pump (not shown in FIG. 1) in the second outflow line 11, a pressure corresponding to the pressure during the first work cycle is established in the exchange vessel 32 during the third work cycle, i.e., during the work cycle in which the lower pressure prevailed in the exchange vessel. Instead of a pump in the outflow line, a hydrostatic pressure already prevailing could be utilized.

The third work cycle follows the second work cycle in the chronological sequence of work cycles.

According to the situation described in conjunction with FIGS. 5 and 6, in which a higher pressure prevails in the exchange vessel during the first work cycle than during the second work cycle, the outflow out of that part of the dialysis fluid circulation that had been connected in the second work cycle is shut off in the third work cycle, i.e., the valve 12 is shut off or closed or kept closed. In addition, the outflow out of that part of the dialysis fluid circulation that had been connected in the first work cycle is opened, i.e., the valve 16 is opened or kept open. Through corresponding control of a pressure-controlled pump (not shown in FIG. 1) in the first outflow line 26, a pressure is established during the third work cycle in the exchange vessel 32, such that it corresponds to the pressure during the second work cycle, i.e., the work cycle in which the lower pressure prevailed in the exchange vessel. Instead of a pump in the outflow line, a hydrostatic pressure that is present could also be utilized.

Figure 8:
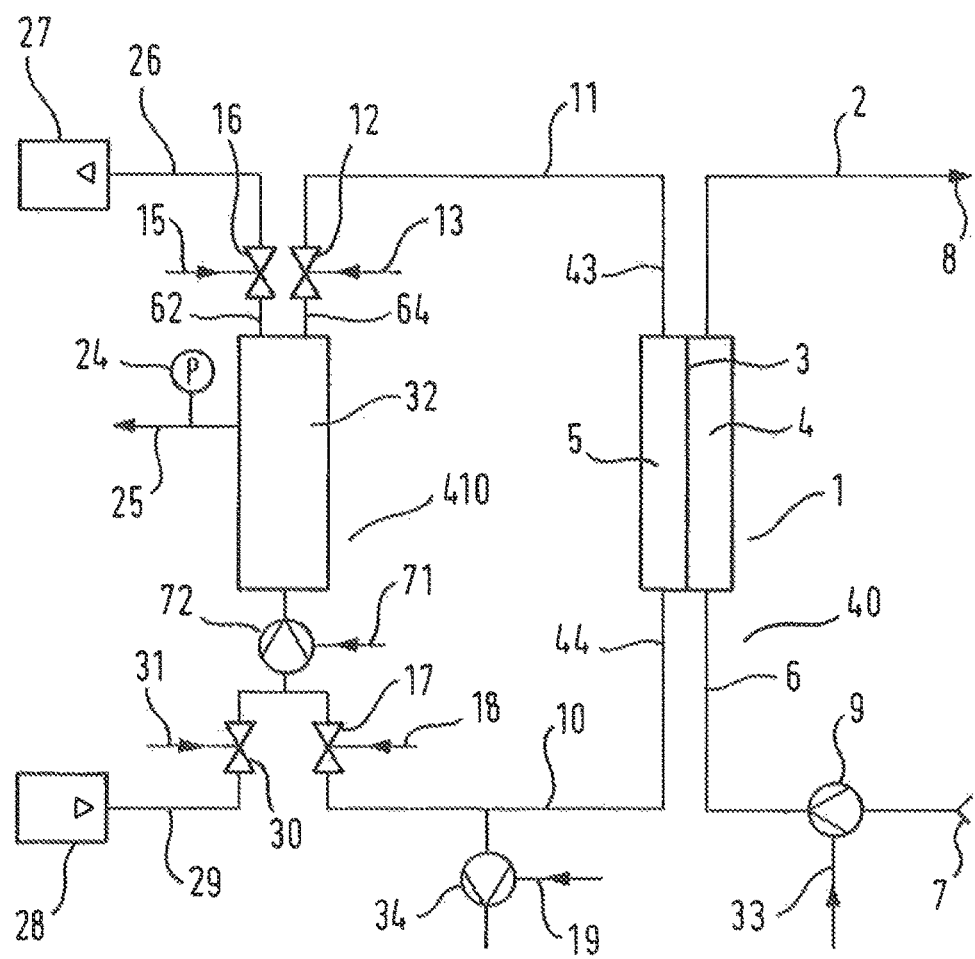
FIG. 8 shows another embodiment of a hemodialysis machine with a balancing device.
Figure 8:
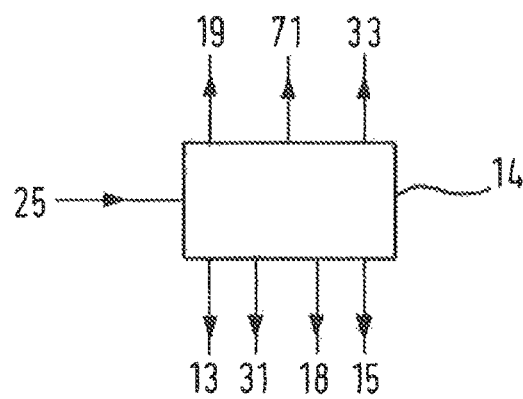

FIG. 8 shows an alternative embodiment of a hemodialysis machine with a balancing device 410. The balancing device 410 diagrammed schematically in FIG. 8 corresponds essentially to the balancing device 41 depicted in FIG. 1, wherein the same or corresponding elements are provided with the same reference numerals. A difference in comparison with the balancing device 41 depicted in FIG. 1 is that, instead of the dialysis fluid pumps 20 and 22, a single dialysis fluid pump 72 which is provided can pump dialysis fluid into the exchange vessel during both the first and second work cycles. The dialysis fluid pump 72 is connected by a control line 71 to the control unit 14 and can be controlled by it. On the one hand, one advantage of this arrangement is that the number of components of the dialysis machine can be reduced due to the use of only one dialysis fluid pump. Another advantage is derived in conjunction with the situation in which the pressure conditions during the dialysis treatment are shifted and the decision is made during the treatment as to whether to proceed as described in conjunction with FIG. 4 or whether to proceed as described in conjunction with FIG. 7. It is possible in this case to switch between these two situations through appropriate control of the valves, so that a single pressure-controlled pump can be controlled in both situations.

Figure 9:
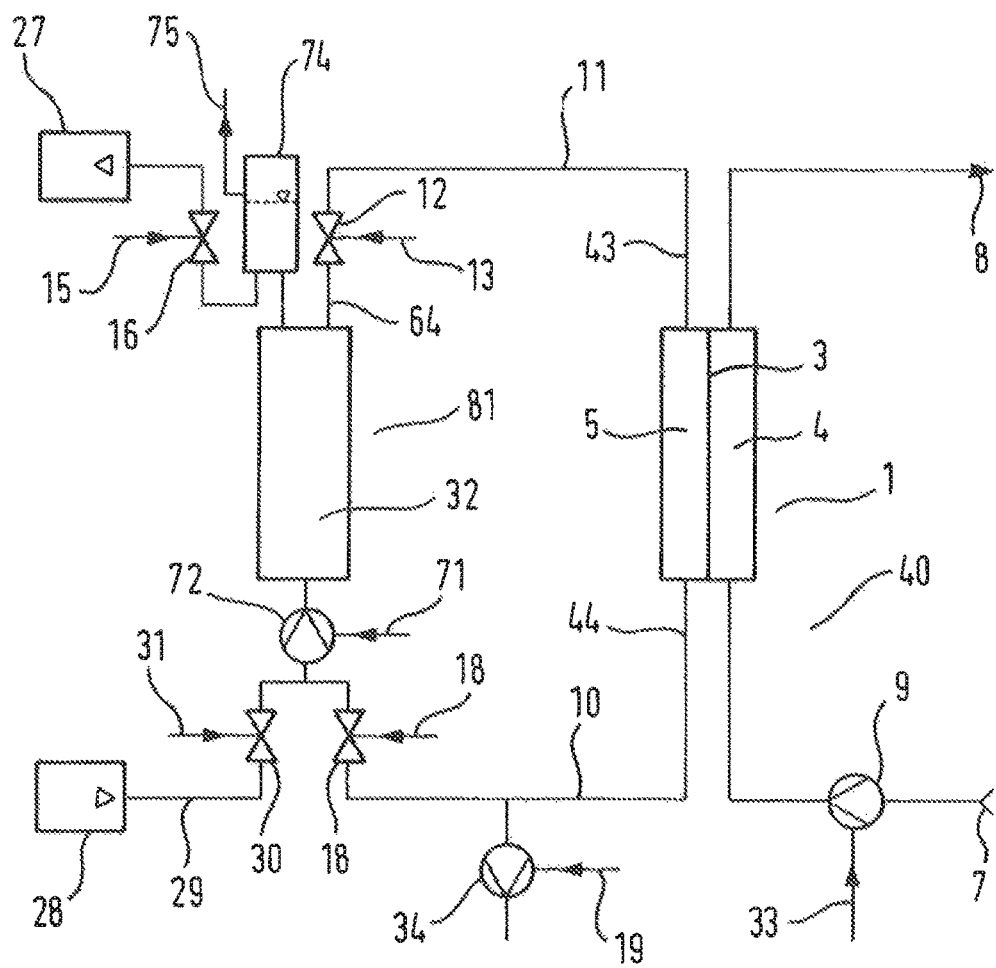
FIG. 9 shows an alternative embodiment of a hemodialysis machine with a balancing device.
Figure 9:
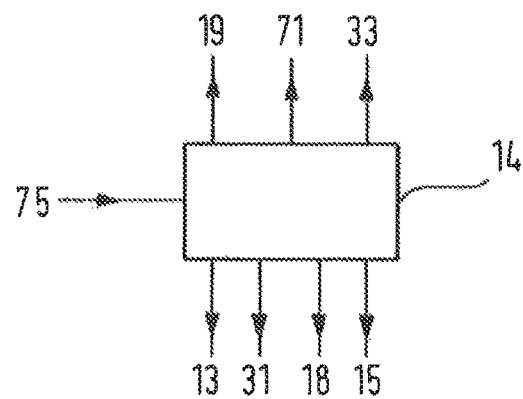

FIG. 9 shows another embodiment of a hemodialysis machine having a balancing device 81. The hemodialysis machine diagrammed schematically in FIG. 9 corresponds essentially to the machine described in conjunction with FIG. 8 with the particular detail that instead of or as a pressure-measuring device 24, an equalizing vessel 74 is provided and is connected at its bottom through a fluid-carrying line to the exchange vessel. In one embodiment, the equalizing vessel is additionally connected to the outflow line 26 and is thus a fluid connection between the exchange vessel 32 and the drain 27. The exchange vessel 74 is sealed toward the top. In the equalizing vessel, there is a gas bubble, which can be compressed as a function of the pressure conditions in the exchange vessel 32. The equalizing vessel 74 also has a level sensor for determining the fluid level, which can be converted to an electric signal and forwarded to the control unit over the data line 75. The fluid level replaces or corresponds to a pressure in the exchange vessel, and the combination of the exchange vessel with the level sensor corresponds to or replaces the pressure sensor 24.

Those skilled in the art will recognize immediately that the combination of an equalizing vessel with a level sensor may also be used in conjunction with the other embodiments described previously.

A third work cycle maybe omitted if it can be assured through the control of the dialysis fluid pump 21, which is in the first dialysis fluid circulation during the first work cycle, and/or the dialysis fluid pump 22, which is in the second dialysis fluid circulation during the second work cycle, that the pressure in the exchange vessel 32 during the first work cycle is essentially the same as the pressure in the second work cycle, wherein in particular toward the end of the first work cycle, the pressure in the exchange vessel 32 is the same as the pressure in the second exchange vessel. The pressure in the exchange vessel during the work cycle, during which the higher pressure prevails in the exchange vessel 32, may be lowered at the end of the work cycle by appropriate control of the dialysis fluid pump, which has a fluid-carrying connection to the exchange vessel 32 in this work cycle.

Figure 10:
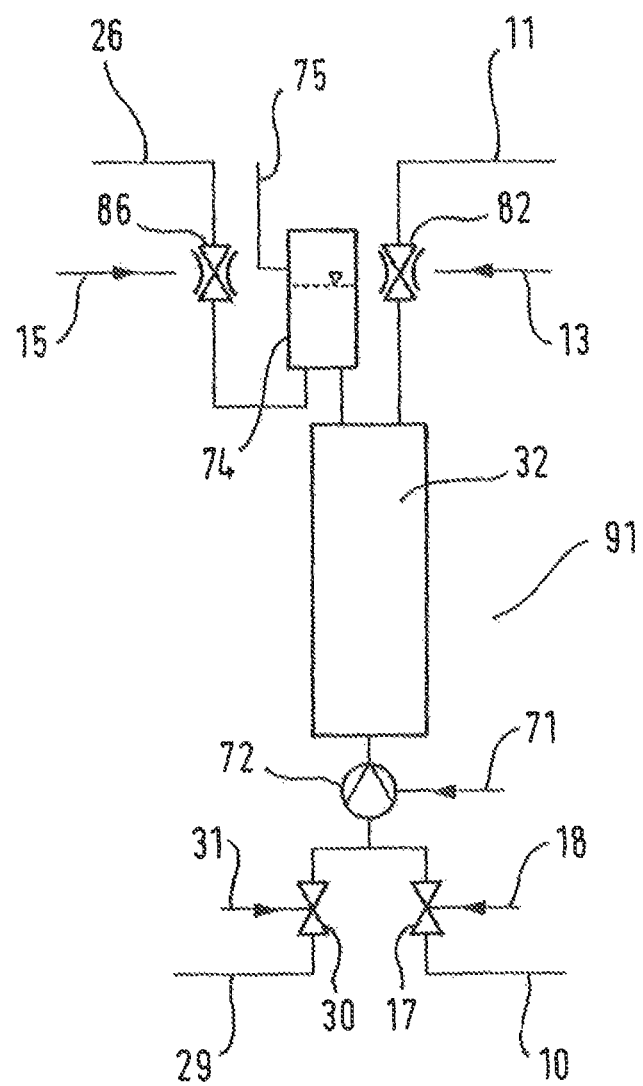
FIG. 10 shows an alternative embodiment of a balancing device.

FIG. 10 shows a further embodiment of the balancing device described in conjunction with FIG. 9. Elements labeled with corresponding reference numerals correspond to those of FIG. 9 to which reference is herewith made instead of repeating the description. The refinement of the balancing device described in conjunction with FIG. 9 lies in the fact that instead of the valves 16 and 12 in the outflow lines 26 and 11, controllable throttle valves 86 and 82 are provided in the outflow lines 26 and 11. In addition to the function of a shut-off organ of the outflow lines 26 and 11, the controllable throttle valves 86 and 82 permit regulation of the flow resistance when the flow through lines 26 and 11 is not shut off. The controllable throttle valves 86, 82 thus permit regulation of the pressure in the equalizing vessel 32 by regulating the flow resistance in the lines 26 and 11. The pressure measured in the exchange vessel can be used to control the throttle valve 86 and the throttle valve 82 in this way, so that at least in one part of the first work cycle, the pressure in the exchange vessel 32, is essentially equal to the pressure in the exchange vessel 32 in at least a part of the second work cycle, wherein this condition should preferably be met toward the end of the respective work cycle. A third work cycle is not necessary in this embodiment. Although the embodiment according to FIG. 10 shows an exchange vessel as a pressure pickup and as a dialysis fluid pump, which can be used in the first work cycle as well as in the second work cycle, the further embodiment depicted in FIG. 10 is not limited to this. Therefore, other pressure pickups can be used according to the diagrams in FIGS. 1 and 8 or a configuration in which different pumps are provided for the first and the second work cycles, according to the configuration described in conjunction with FIG. 1. A third work cycle is not necessary in operation of the balancing device described in conjunction with FIG. 10 as long as the pressure in the exchange vessel 32 is adjusted with the help of regulable throttle valves 86 and 82, so that the same pressure prevails in the exchange vessel 32 toward the end of the first work cycle as toward the end of the second work cycle. Instead of the regulable throttle valves 86, 82, throttles may also be provided in addition to the valves in the shut-off lines 11 and 26 and they fulfill a throttle function independently of a function of a shut-off organ. The pressure in the exchange vessel 32 may also be controlled by a combined use of the throttle valves 86, 82 and the one or more pressure-controlled pumps in the inlet line(s) to the exchange vessel 32, wherein the pressure is equalized between the first and second work cycles, as described above.

The invention claimed is:

1. A balancing device for balancing between an inflow into a blood treatment unit, comprising: at least one exchange vessel, a first inlet line leading to the exchange vessel for carrying a fluid out of a fluid source into the exchange vessel and a first outflow line departing from the exchange vessel for carrying the fluid out of the exchange vessel into a drain, a second outflow line departing from the exchange vessel for carrying the fluid out of the exchange vessel into the treatment unit and a second inlet line leading to the exchange vessel for carrying the fluid out of the treatment unit into the exchange vessel, at least one of a means for conveying fluid into the exchange vessel and/or out of the exchange vessel and at least one of a means for interrupting fluid flow into the exchange vessel and/or out of the exchange vessel, a pressure pick up for sensing pressure in the exchange vessel, a control unit connected to the pressure pickup, for controlling the means for conveying fluid and the means for interrupting fluid, wherein the control unit is configured to form, in a first work cycle of successive work cycles, a first fluid circulation wherein the fluid from the exchange vessel flows into the drain and is replaced by a fresh fluid from the fluid source and to form, in a second work cycle of the successive work cycles, a second fluid circulation wherein the fresh fluid from the exchange vessel flows into the treatment unit and is replaced by the fluid from the treatment unit, and to effect a pressure equalization between the first and second work cycles.

2. The balancing device according to claim 1, further comprising a first throttle for controlling the fluid flow through the first outflow line and a second throttle for controlling the fluid flow through the second outflow line, wherein the control unit is configured for controlling the first and second throttles in order that at least in one part of the first work cycle the pressure in the exchange vessel is essentially equal to the pressure in the exchange vessel at least in one part of the second work cycle.

3. The balancing device according to claim 1, wherein the means for conveying fluid is connected to the first and second inlet lines or to the first and second outflow lines through a fluid-carrying line, such that the means for conveying fluid can convey fluid during the first work cycle and during the second work cycle.

4. The balancing device according to claim 1, wherein the control unit is configured to control the means for conveying fluid using a test signal of the pressure pickup.

5. The balancing device according to claim 4, wherein the means for conveying fluid is a pressure-controlled pump.

6. The balancing device according to claim 5, wherein the pressure-controlled pump is an impeller pump or a diaphragm pump.

7. The balancing device according to claim 1, wherein the pressure pickup is designed as a gas-filled equalizing vessel, in fluid connection with the exchange vessel, and wherein a measurement means is provided for determining the fluid level in the equalizing vessel, and wherein the fluid level is a measure of the pressure in the exchange vessel.

8. The balancing device according to claim 1, wherein the exchange vessel does not have a constant volume when there is a change in the pressure in the exchange vessel.

9. The balancing device according to claim 1, wherein the exchange vessel is designed as a disposable item or as part of a disposable item.

10. A medical treatment device having a balancing device according to claim 1.

11. The medical treatment device according to claim 10, designed as a dialysis machine.

12. A method for balancing between an inflow into a blood treatment unit of a medical treatment device and an outflow out of the blood treatment unit, comprising; in a first work cycle of successive work cycles, a first fluid circulation is formed, wherein a fluid flows out of an exchange vessel into an outflow through a first outflow line, and a fresh fluid flows out of a fluid source through a first inlet line into the exchange vessel, in a second work cycle of the successive work cycles, a second fluid circulation is formed, wherein the fresh fluid from the exchange vessel flows out of the exchange vessel into the blood treatment unit through a second outflow line and is replaced by a fluid from the blood treatment unit through a second inlet line, the pressure in the exchange vessel is measured during the first and second work cycles, and at least one of a means for conveying fluid into the exchange vessel and/or out of the exchange vessel and at least one of a means for interrupting fluid flow into the exchange vessel and/or out of the exchange vessel are controlled to effect an equalization of pressure between the first and second work cycles.

13. A method for balancing fluids between an inflow into a blood treatment unit of a medical treatment device and an outflow out of the blood treatment unit, comprising; a first fluid circulation wherein a fluid flows out of an exchange vessel into an outflow through a first outflow line formed in a first work cycle of successive work cycles, and a fresh fluid flows out of a fluid source into the exchange vessel through a first inlet line, in a second work cycle of the successive work cycles, a second fluid circulation is formed, wherein the fresh fluid flows out of the exchange vessel and into the blood treatment unit through a second outflow line and is replaced by a fluid from the blood treatment unit through a second inlet line, the pressure in the exchange vessel is measured during the first and second work cycles, and the measured pressure is used to control a throttle in one of the outflow lines, so that the pressure in the exchange vessel in at least a portion of the first work cycle is essentially the same as the pressure in the exchange vessel in at least a portion of the second work cycle.

* * * * *